United States Patent
Hishida et al.

(10) Patent No.: US 9,824,435 B2
(45) Date of Patent: Nov. 21, 2017

(54) IMAGE ANALYZING APPARATUS AND PROGRAM

(71) Applicants: IHI CORPORATION, Koto-ku (JP); The University of Tokyo, Bunkyo-ku (JP)

(72) Inventors: HIroyuki Hishida, Koto-ku (JP); Koichi Inagaki, Koto-ku (JP); Takeshi Nakamura, Koto-ku (JP); Yuta Yamauchi, Bunkyo-ku (JP); Hiromasa Suzuki, Bunkyo-ku (JP); Takashi Michikawa, Bunkyo-ku (JP); Yutaka Ohtake, Bunkyo-ku (JP)

(73) Assignees: IHI CORPORATION, Koto-ku (JP); The University of Tokyo, Bunkyo-ku (JP)

(*) Notice: Subject to any disclaimer, the term of this patent is extended or adjusted under 35 U.S.C. 154(b) by 58 days.

(21) Appl. No.: 15/025,983

(22) PCT Filed: Sep. 29, 2014

(86) PCT No.: PCT/JP2014/075954
§ 371 (c)(1),
(2) Date: Mar. 30, 2016

(87) PCT Pub. No.: WO2015/046534
PCT Pub. Date: Apr. 2, 2015

(65) Prior Publication Data
US 2016/0247271 A1    Aug. 25, 2016

(30) Foreign Application Priority Data
Sep. 30, 2013 (JP) .................................. 2013-204574

(51) Int. Cl.
*G06K 9/00* (2006.01)
*G06T 7/00* (2017.01)
(Continued)

(52) U.S. Cl.
CPC ............ *G06T 7/0004* (2013.01); *G01B 15/00* (2013.01); *G01N 23/04* (2013.01); *G01N 23/046* (2013.01);
(Continued)

(58) Field of Classification Search
CPC ......... G06T 7/0004; G06T 2207/10012; G06T 2207/10081; G06T 2207/30124;
(Continued)

(56) References Cited

U.S. PATENT DOCUMENTS

| | | | |
|---|---|---|---|
| 6,526,305 B1* | 2/2003 | Mori ................ | G01R 33/56341 128/920 |
| 2008/0122440 A1* | 5/2008 | Sakai ................ | G01R 33/56341 324/309 |
| 2010/0135560 A1* | 6/2010 | Embleton ........ | G01R 33/56341 382/131 |

FOREIGN PATENT DOCUMENTS

| | | |
|---|---|---|
| JP | 2012-002547 A | 1/2012 |
| WO | 2014/080622 A1 | 5/2014 |

OTHER PUBLICATIONS

Blanc, Rémi, et al. "Fiber orientation measurements in composite materials." Composites Part A: applied science and manufacturing 37.2 (2006): 197-206.*

(Continued)

*Primary Examiner* — Li Liu
(74) *Attorney, Agent, or Firm* — Oblon, McClelland, Maier & Neustadt, L.L.P.

(57) ABSTRACT

Proposed are an image analyzing apparatus and program in which the orientation of fiber bundles can be easily analyzed from a three-dimensional image of CMC. Provided is an image analyzing apparatus for analyzing an orientation of a fiber bundle from a three-dimensional image of a fiber-reinforced composite material, comprising an input unit which inputs the three-dimensional image, a binarization (Continued)

processing unit which binarizes the input three-dimensional image and acquires a binary image, an orientation estimation processing unit which estimates each orientation of foreground pixels in the binary image based on an orientation detection filter having a parameter for causing a shape of a detected cross section to have anisotropy, a center extraction processing unit which extracts center pixels showing a center of the fiber bundle from a foreground pixel group, in which the orientation thereof was estimated, based on the orientation detection filter, a fiber bundle connection processing unit which deems center pixels having a same or similar orientation to be a same fiber bundle with regard to the extracted center pixel group, and connects the center pixels indicating the same fiber bundle, and a meander determination processing unit which calculates a meandering amount of the connected center pixel group indicating the same fiber bundle.

10 Claims, 8 Drawing Sheets

(51) Int. Cl.
*G01N 23/04* (2006.01)
*G01B 15/00* (2006.01)
*G06K 9/46* (2006.01)

(52) U.S. Cl.
CPC ..... *G06K 9/4604* (2013.01); *G01N 2223/419* (2013.01); *G06T 2207/10012* (2013.01); *G06T 2207/10081* (2013.01); *G06T 2207/30124* (2013.01)

(58) Field of Classification Search
CPC .......... G06T 2207/30108; G01B 15/00; G01N 23/046; G01N 2223/419; G06K 9/4604; G06K 9/52; G06K 9/6215; G06K 9/6267
See application file for complete search history.

(56) References Cited

OTHER PUBLICATIONS

Gadala-Maria, F., and F. Parsi. "Measurement of fiber orientation in short-fiber composites using digital image processing." Polymer Composites 14.2 (1993): 126-131.*
Toshihiro Shinohara, et al., "Extraction of Yarn Positional Information from a Three-dimensional CT Image of Textile Fabric using Yarn Tracing with a Filament Model for Structure Analysis", Textile Research Journal, vol. 80, No. 7, 2010, pp. 623-630, (9 pages).
Toshihiro Shinohara, et al., "Analysis of Knitted Fabric Structure using 3-D Voxel Data of X-ray CT Images", SICE, vol. 41, No. 11, Nov. 2005, pp. 879-885, with partial English translation, (22 pages).
Yuta Yamauchi, et al., "A Basic Research for Recognition of Fibrous Structure by CT Volume Image", JSPE, 2012, pp. 269-270, with partial English translation, (8 pages).
International Search Report dated Dec. 2, 2014 for PCT/JP2014/075954 filed on Sep. 29, 2014.
Extended European Search Report dated Apr. 12, 2017 in Patent Application No. 14847522.1.
Hrishikesh Bale, et al., "Characterizing Three-Dimensional Textile Ceramic Composites Using Synchrotron X-Ray Micro-Computed-Tomography" Journal of the American Ceramic Society, vol. 95, No. 1, XP055331937, Jan. 31, 2012, pp. 392-402.
Oliver Wirjadi, et al., "Applications of Anisotropic Image Filters for Computing 2D and 3D-Fiber Orientations" Proceedings of the 10th European Conference in Image Analysis and Stereology (ECS10), XP055359380, Jun. 29, 2009, pp. 1-6.

* cited by examiner

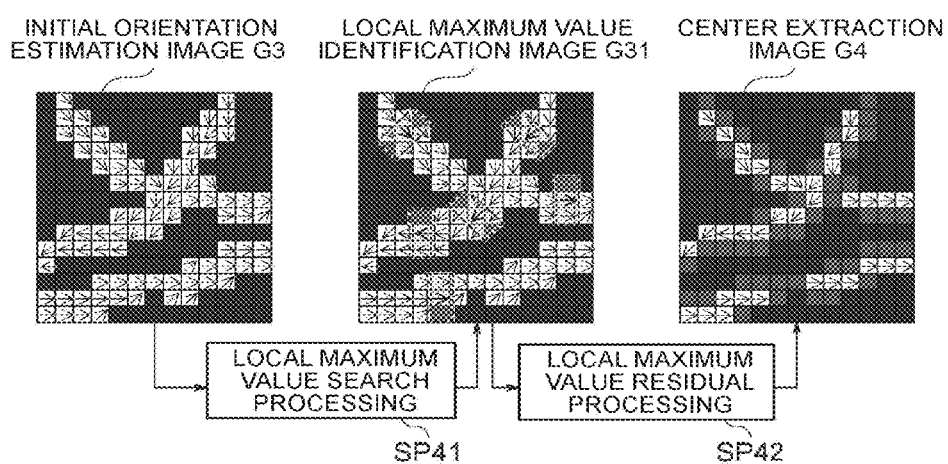
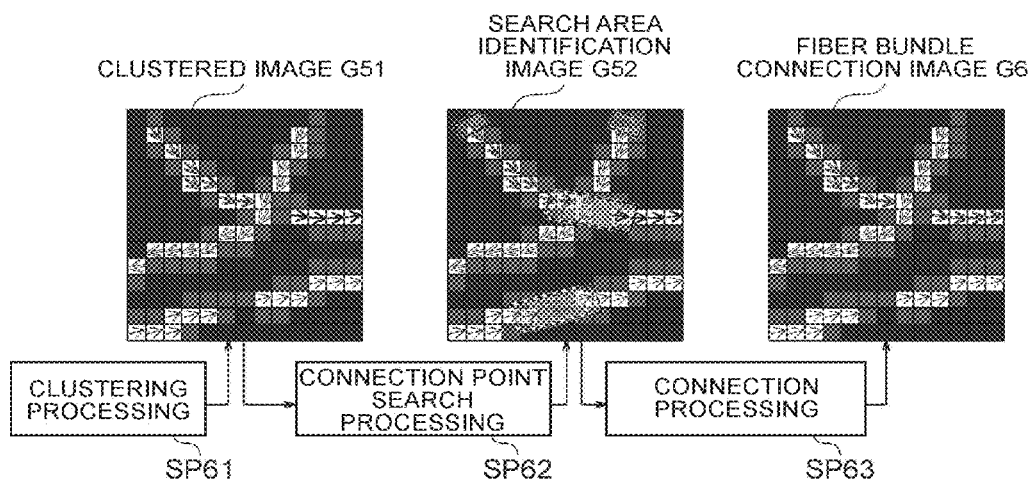

IMAGE ANALYZING APPARATUS AND PROGRAM

TECHNICAL FIELD

The present disclosure relates to an image analyzing apparatus and program, and in particular can be suitably applied to an image analyzing apparatus and program capable of analyzing the orientation of a fiber bundle contained in a fiber-reinforced composite material.

BACKGROUND ART

In recent years, the development of ceramic matrix composites (CMC) as one type of fiber-reinforced composite material is being promoted. CMC is a composite material in which ceramic fiber is reinforced with a matrix, and is characterized in being light and having superior heat resistance properties. By leveraging these characteristics, for instance, the possibility of using CMC in aircraft engine parts is being considered, and the practical application thereof is currently being sought. Note that the use of CMC as aircraft engine parts is expected to considerably improve the fuel economy.

The general process of forming CMC is as follows. Foremost, roughly several hundred ceramic fibers are bundled to prepare a fiber bundle, and the prepared fiber bundles are woven into a fabric. As the weaving method of fiber bundles, for instance, known are methods referred to as three-dimensional weaving and plain weaving. Three-dimensional weaving is a method of weaving the fiber bundles from three directions (XYZ directions) to prepare a fabric, and plain weaving is a method of weaving the fiber bundles from two directions (XY directions) to prepare a fabric.

After the fabric is prepared, a matrix is formed via CVI (Chemical Vapor Infiltration) and PIP (Polymer Impregnation and Pyrolysis), and CMC is thereafter formed by ultimately performing machining and surface coating. Here, the orientation of the fiber bundles in the formed CMC will considerably affect the strength of that CMC.

In other words, if the fiber bundles are meandering at a location where they should actually form a straight line, generally deviating from the reference axis whether they should actually be positioned, or ruptured midway, the strength of CMC will considerably deteriorate. Meanwhile, when the fiber bundles are appropriately arranged in alignment in a specific direction without any meandering, deviation or rupture, CMC will yield high strength and superior heat resistance properties. Thus, in order to confirm whether the strength of the formed CMC is sufficient, it is important to evaluate the orientation of the fiber bundles.

PTL 1 discloses an orientation analysis method of binarizing a sliced image of a resin molding and acquiring a binary image, subjecting the acquired binary image to Fourier transformation to acquire a power spectrum image, and determining the main axial direction of an oval that is perpendicular to the oval drawn based on the acquired power spectrum image as the orientation of the filler (fibers) contained in the resin molding.

Moreover, NPL 1 discloses a technology of imaging a fabric produced by weaving fiber bundles using an X-ray CT device and acquiring an X-ray CT image, and performing a calculation using a special filter function with regard to the acquired X-ray CT image in order to analyze the orientation of each and every fiber configuring the fiber bundle.

CITATION LIST

Patent Literature

[PTL 1] Japanese Patent Application Publication No. 2012-2547

Non-Patent Literature

[NPL 1] T. Shinohara, J. Takayama, S. Ohyama, and A. Kobayashi, "Extraction of Yarn Positional Information from a Three-dimensional CT Image of Textile Fabric using Yarn Tracing with a Filament Model for Structure Analysis", Textile Research Journal, Vol. 80, No. 7, pp. 623-630 (2010)

SUMMARY

Technical Problem

Nevertheless, with the technology described in PTL 1, it is possible to only obtain the analysis result of the orientation direction of one direction regarding the orientation of the filler (fibers) contained in the sliced image. Accordingly, for instance, when the fiber bundles are orientated in a plurality of directions such as when formed via three-dimensional weaving or plain weaving, it is not possible to obtain the orientation of the respective fiber bundles as the analysis result. Moreover, it is not possible to analyze whether the fiber bundles are appropriately arranged in alignment in a specific direction without any meandering, deviation or rupture.

Moreover, with the technology described in NPL 1, it is necessary to acquire a high resolution X-ray CT image of a level which enables the distinction of each and every fiber configuring the fiber bundles. In the foregoing case, the imaging time required for obtaining the X-ray CT image will be prolonged, and this is impracticable since this technology cannot be used for product inspection. Moreover, while NPL 1 is a technology that is effective for fibers having an oval cross section, it cannot be used as is for analyzing the orientation of fiber bundles having a flat cross section. Furthermore, there is also a problem in that the operation is complicated since the starting point of the respective fibers in the X-ray CT image needs to be input.

The present disclosure was devised in view of the foregoing problems, and proposes an imaging analyzing apparatus and program in which the orientation of fiber bundles can be easily analyzed from a three-dimensional image of CMC.

Solution to Problem

In order to achieve the foregoing object, the present disclosure provides an image analyzing apparatus for analyzing an orientation of a fiber bundle from a three-dimensional image of a fiber-reinforced composite material, comprising an input unit which inputs the three-dimensional image, a binarization processing unit which binarizes the input three-dimensional image and acquires a binary image, an orientation estimation processing unit which estimates each orientation of foreground pixels in the binary image based on an orientation detection filter having a parameter for causing a shape of a detected cross section to have anisotropy, a center extraction processing unit which extracts center pixels showing a center of the fiber bundle from a foreground pixel group, in which the orientation thereof was estimated, based on the orientation detection filter, a fiber bundle connection processing unit which deems center pixels having a same or similar orientation to be a same fiber bundle with regard to the extracted center pixel group, and connects the center pixels indicating the same fiber bundle, and a meander determination processing unit which calculates a meandering amount of the connected center pixel group indicating the same fiber bundle.

Moreover, in order to achieve the foregoing object, the present disclosure provides a program for analyzing an orientation of a fiber bundle from a three-dimensional image of a fiber-reinforced composite material, wherein the program causes a computer to execute a first step of inputting the three-dimensional image, a second step of binarizing the input three-dimensional image and acquiring a binary image, a third step of estimating each orientation of foreground pixels in the binary image based on an orientation detection filter having a parameter for causing a shape of a detected cross section to have anisotropy, a fourth step of extracting center pixels indicating a center of the fiber bundle from a foreground pixel group, in which the orientation thereof was estimated, based on the orientation detection filter, a fifth step of deeming center pixels having a same or similar orientation to be a same fiber bundle with regard to the extracted center pixel group, and connecting the center pixels indicating the same fiber bundle, and a sixth step of calculating a meandering amount of the connected center pixel group indicating the same fiber bundle.

Effects

According to the present disclosure, the orientation of fiber bundles can be easily analyzed from a three-dimensional image of CMC.

BRIEF DESCRIPTION OF DRAWINGS

FIG. 6 is a detailed flowchart of the center extraction processing.

FIG. 7 is a detailed flowchart of the fiber bundle connection processing.

DESCRIPTION OF EMBODIMENTS

An embodiment of the present disclosure is now explained in detail with reference to the drawings.

(1) Overall Configuration

Figure 1:
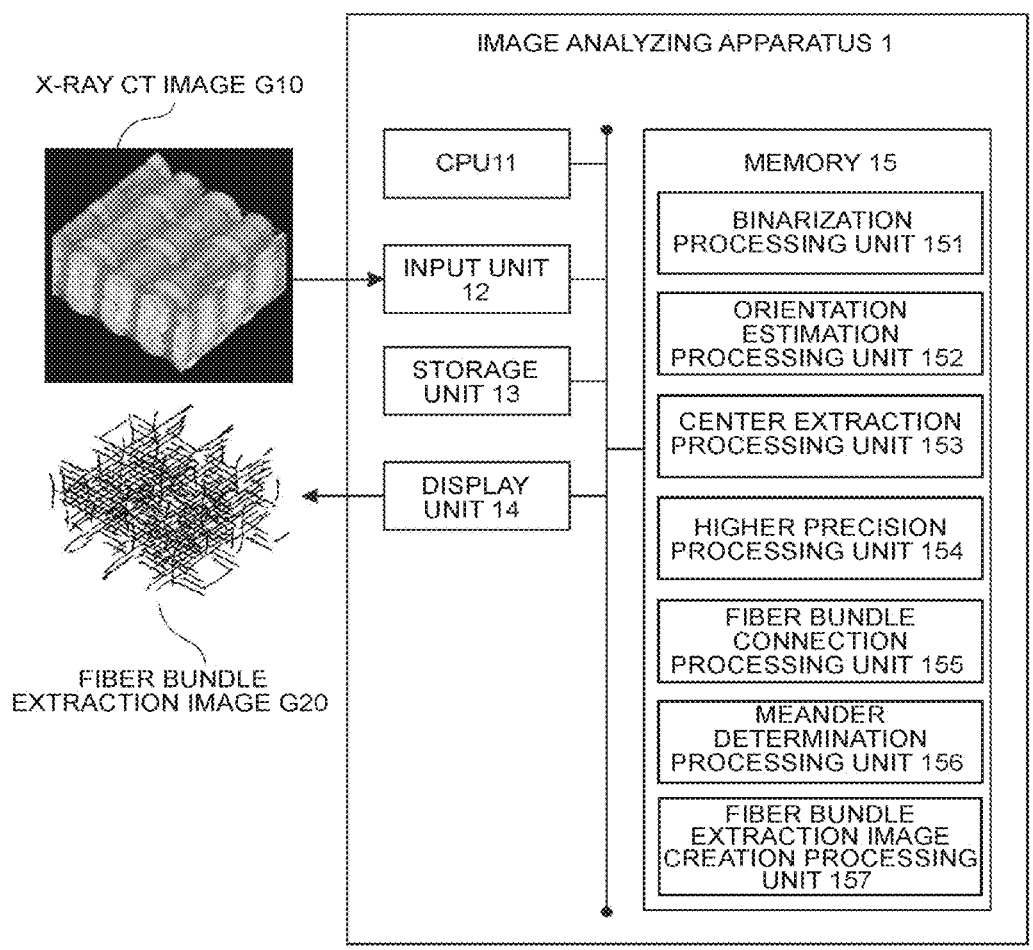
FIG. 1 is an overall configuration diagram of the image analyzing apparatus in this embodiment.

FIG. 1 shows the overall configuration of an image analyzing apparatus 1 in this embodiment. The image analyzing apparatus 1 is configured by comprising a CPU (Central Processing Unit) 11, an input unit 12, a storage unit 13, a display unit 14 and a memory 15.

The CPU 11 is a processor that coordinates with various programs stored in the memory 15 and controls the operation of the image analyzing apparatus 1. The input unit 12 is an interface for receiving inputs from a user and is configured, for example, from a keyboard or a mouse. Moreover, the input device 12 in this embodiment is also an interface for inputting an X-ray CT image G10 of the fabric configuring CMC (Ceramic Matrix Composites).

Here, CMC refers to a fiber-reinforced composite material that is formed by bundling roughly several hundred ceramic fibers to prepare a fiber bundle, weaving the prepared fiber bundles into a fabric, thereafter coating the fiber surface with carbon or the like, and performing CVI (Chemical Vapor Infiltration) and PIP (Polymer Impregnation and Pyrolysis) in order to form a matrix.

As the weaving method of fiber bundles, for instance, known are methods referred to as three-dimensional weaving and plain weaving. Three-dimensional weaving is a method of weaving the fiber bundles from three directions (XYZ directions) to prepare a fabric, and plain weaving is a method of weaving the fiber bundles from two directions (XY directions) to prepare a fabric.

In this embodiment, a fabric prepared via three-dimensional weaving or plain weaving (or other weaving methods) or CMC formed from such fabric is imaged, and orientation of the fiber bundles is automatically analyzed from the obtained X-ray CT image G10. The orientation of the fiber bundles configuring the fabric considerably affects the strength of that CMC. Thus, the strength of CMC formed from such fabric can be evaluated based on the results of the automatic analysis.

Note that, generally speaking, "orientation" is a term that means to arrange in alignment in a specific direction, or such arranged state, but in this embodiment the term "orientation" is used as a term that means to arrange in alignment in a specific direction without deviation or rupture, or such arranged state. Moreover, there may be cases where the arranged direction is explained by being described as "orientation direction" or simply as "orientation".

Returning to FIG. 1, the storage unit 13 is a storage medium for storing the X-ray CT image G10 input from the input unit 12 and the images that are created by processing and correcting the X-ray CT image G10 via various types of image processing. The display unit 14 is a display device such as an LCD (Liquid Crystal Display) for displaying the X-ray CT image G10 and the images created through processing and correction via various types of image processing. For example, the display unit 14 displays, on a display screen, a fiber bundle extraction image G20 as the analysis result of automatically analyzing the orientation of the fiber bundles from the X-ray CT image G10.

The memory 15 is a storage medium for storing various programs that are used for executing image analysis processing by coordinating with the CPU 11. The various programs include a binarization processing unit 151, an orientation estimation processing unit 152, a center extraction processing unit 153, a higher precision processing unit 154, a fiber bundle connection processing unit 155, a meander determination processing unit 156 and a fiber bundle extraction image creation processing unit 157. The image analysis processing (FIG. 2) to be executed by these various programs and the details of the respective processes in the image analysis processing (FIG. 3A to FIG. 9) will be described later.

(2) Overall Processing

Figure 2:
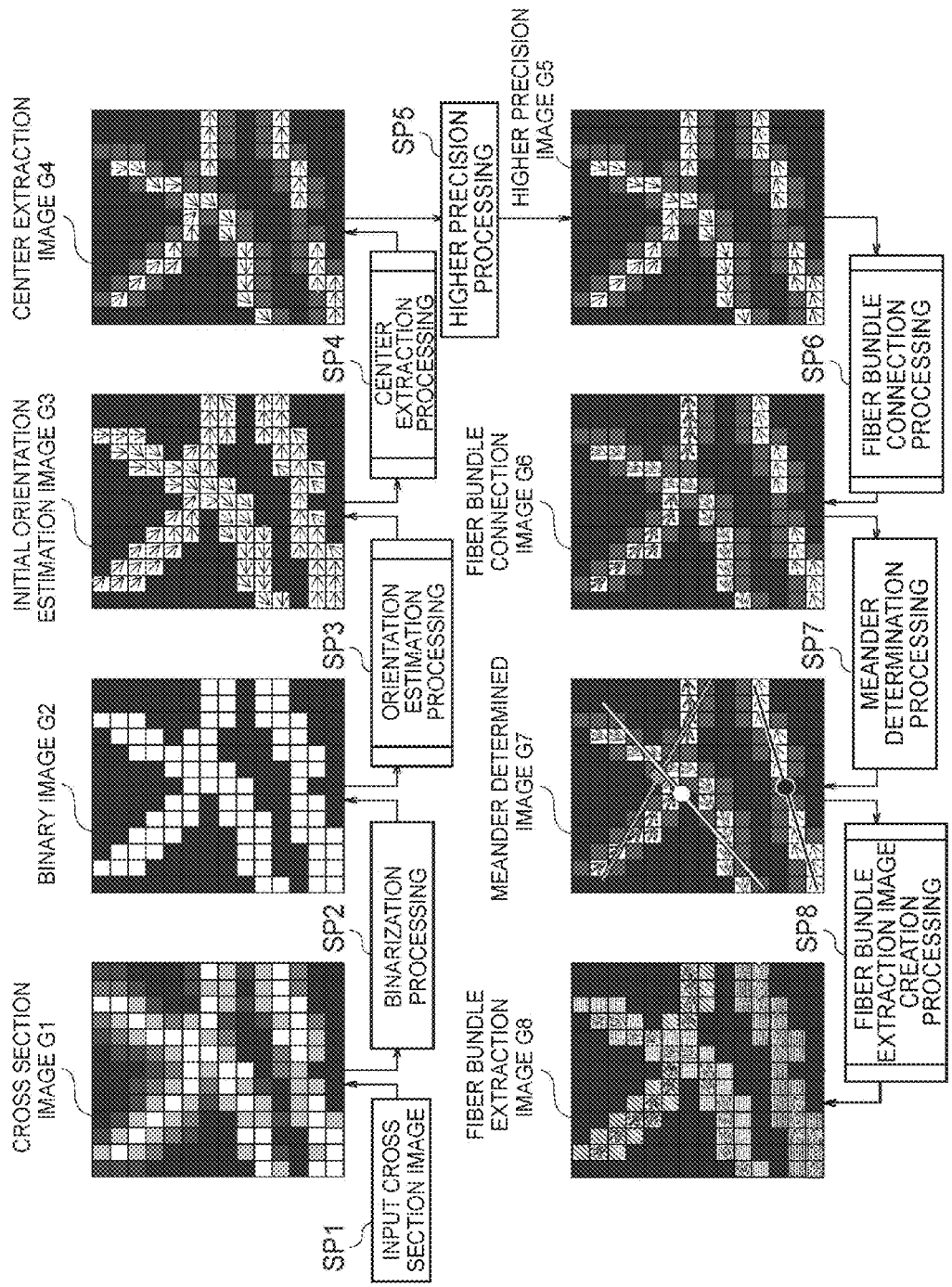
FIG. 2 is a flowchart showing the image analysis processing.

FIG. 2 shows the processing routine of the image analysis processing in this embodiment. The image analysis processing is executed through the coordination of the CPU 11 and the various programs stored in the memory 15 triggered by the input unit 12 receiving an execution instruction from a user. For the sake of convenience in the ensuing explanation, the explanation is provided with the various programs as the subject of processing.

Foremost, the binarization processing unit 151 inputs the X-ray CT image G10 (SP1). While the X-ray CT image G10 is a three-dimensional image, for the sake of explanation, two-dimensional diagrams are used in FIG. 2 and FIG. 6. Next, the binarization processing unit 151 executes binarization processing to the input X-ray CT image G10, and creates a binary image G2 showing a fiber bundle in the foreground (SP2).

Next, the orientation estimation processing unit 152 executes orientation estimation processing to the plurality of foreground pixels (foreground pixel group) shown in the binary image G2 by using the ASF (Anisotropic Shinohara Filter) function, which is prepared in advance in this embodiment, and creates an initial orientation estimation image G3 showing the estimated orientation of each pixel in the foreground pixel group (SP3).

While the details of ASF will be described later (FIG. 3A to FIG. 4B), ASF is a filter that expanded the conventionally known Shinohara Filter, and is a filter in which a parameter for yielding anisotropy has been added to the Shinohara Filter. By using this ASF, the orientation of oval or rectangular objects (for example, fiber bundles) can be detected in addition to the orientation of objects (for example, fibers) having a circular cross section.

Next, the center extraction processing unit 153 executes center extraction processing to the foreground pixel group shown in the initial orientation estimation image G3 by using ASF in order to extract only the center pixels, and creates a center extraction image G4 showing the thinned foreground pixel group (SP4).

Next, the higher precision processing unit 154 executes higher precision processing to each pixel in the foreground pixel group shown in the center extraction image G4 in order to make minor amendments to the orientation estimated in step SP3, and creates a higher precision image G5 showing orientations of higher precision (SP5).

Next, the fiber bundle connection processing unit 155 deems the foreground pixels showing a direction having a same or similar orientation (orientation within a predetermined angular range) to be the foreground pixels showing the same fiber bundle with regard to the foreground pixel group shown in the higher precision image G5, executes fiber bundle connection for connecting the foreground pixels showing the same fiber bundle, and thereby creates a fiber bundle connection image G6 (SP6).

Next, the meander determination processing unit 156 executes meander determination processing, which calculates the meandering amount by using the least-squares method, to the respective fiber bundles shown in the fiber bundle connection image G6, and creates a meander determined image G7 showing an approximate straight line for the determining the existence of any meandering (SP7). Moreover, the fiber bundle extraction image creation processing unit 157 executes fiber bundle extraction image creation processing of adding a volume (pixels) to the respective fiber bundles shown in the fiber bundle connection image G6 or the meander determined image G7, and creates a fiber bundle extraction image G8 showing the actual fiber bundle width (SP8).

After each processing of step SP1 to SP8 described above is executed, the CPU 11 ends the image analysis processing.

(3) Details of Processing

Details of the respective processes (SP3 to SP8) explained with reference to FIG. 2 are now explained with reference to FIG. 3A to FIG. 9, and with reference to the calculation formulas (Formula 1 to Formula 4). Note that, since the input processing (SP1) and the binarization processing (SP2) of the X-ray CT image G10 are based on general techniques, the explanation thereof is omitted.

Figure 3A:
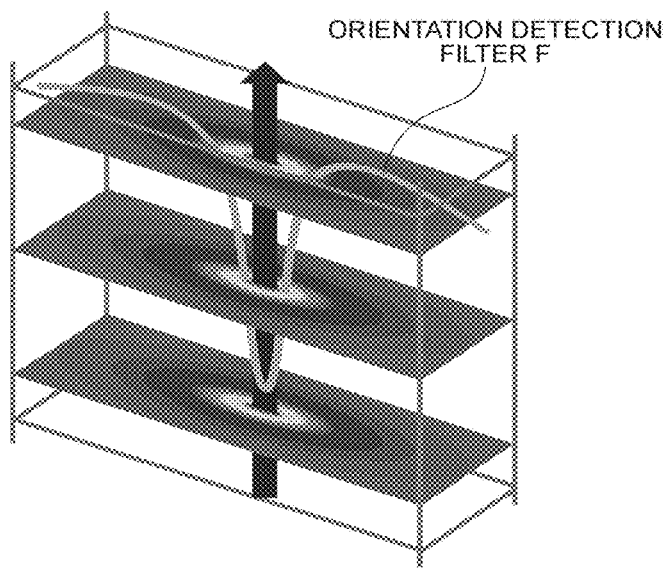
FIG. 3A is a conceptual configuration diagram of an orientation detection filter.

FIG. 3A shows the conceptual configuration of the ASF (hereinafter referred to as the "orientation detection filter F") function. The orientation detection filter F is used for estimating the orientation of each pixel in the foreground pixel group in the orientation estimation processing (SP3). Moreover, the orientation detection filter F is used for extracting the center pixels from the foreground pixel group in the center extraction processing (SP4).

The orientation detection filter F is, as described above, a filter in which a parameter for yielding anisotropy has been added to the Shinohara Filter. The orientation detection filter F can change the shape of the detected cross section into an arbitrary shape by changing the parameter for yielding anisotropy. Here, a parameter for yielding anisotropy in the XY directions when the direction of the fiber bundle is the Z direction is adopted so that the orientation of a fiber bundle having an oval cross section can be detected. The orientation detection filter F is expressed with following Formula 1.

TABLE 1

$$h_{\phi,\theta,\psi}(u) = -2\exp\left\{(-(s+1)\log 2)\left(\frac{u'^2_x}{\sigma^2_x} + \frac{u'^2_y}{\sigma^2_y}\right)\right\} + \exp\left\{(-(s+1)\log 2)\left(\frac{u'^2_x}{\sigma^2_x} + \frac{u'^2_y}{\sigma^2_y}\right)\right\} \quad (1)$$

$\phi,\theta,\psi$: Attitude control angles of orientation detection filter
u: parameter of detected cross section
s: Adjustment parameter (s + 1 > 0)

Figure 3B:
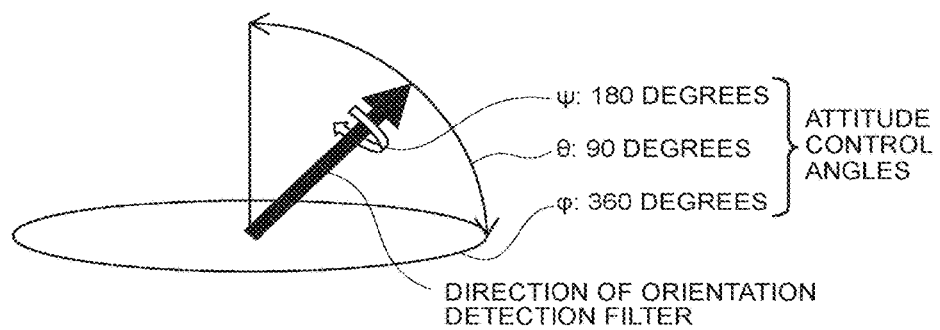
FIG. 3B is a conceptual configuration diagram of attitude control angles.

FIG. 3B shows the conceptual configuration of the attitude control angles of the orientation detection filter F. As also shown in foregoing Formula 1, the orientation detection filter F has, as variables, two angles ($\phi$, $\theta$) for designating the axial direction of the filter, and one angle ($\psi$) for designating the amount of rotation upon rotating the filter with the axial direction as the axis of rotation. Here, these three angles ($\phi$, $\theta$, $\psi$) are referred to as the attitude control angles of the orientation detection filter F. When the filter axial direction and the rotating angle that are determined by the attitude control angles coincide with the orientation direction of the fiber bundle, the output value described later becomes maximum. By utilizing these characteristics, the orientation of the fiber bundle can be detected.

Figure 4A:
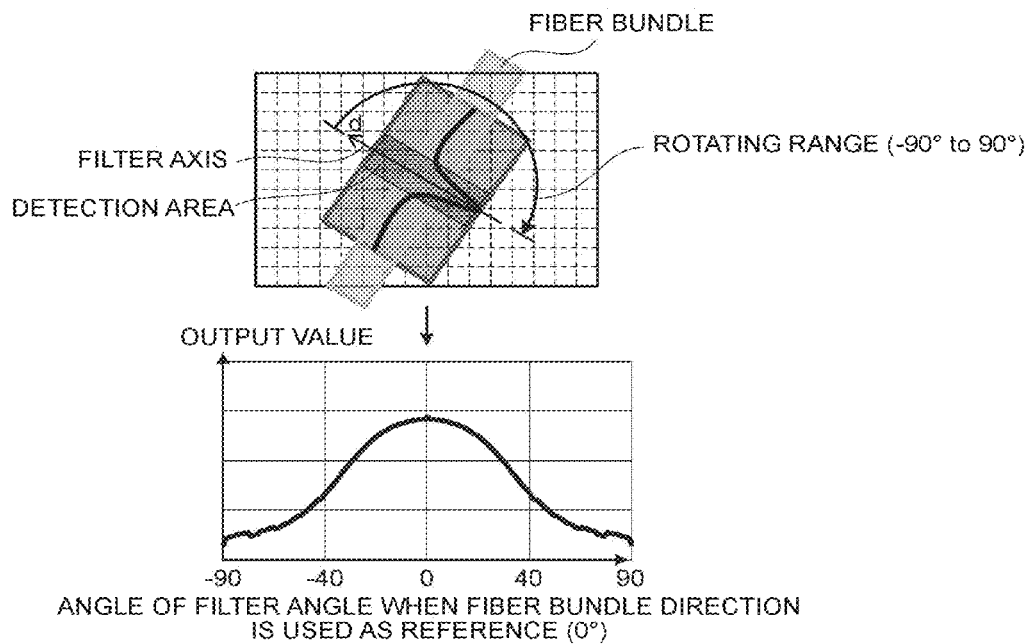
FIG. 4A is a conceptual diagram of the operation for detecting the direction of the fiber bundle.

FIG. 4A shows a conceptual diagram of the operation upon detecting the direction of the fiber bundle by using the orientation detection filter F. As shown in FIG. 4A, when the fiber bundle is facing a direction that is obliquely upward and rightward, operation is performed so as to rotate the filter axis of the orientation detection filter F within a range of, for example, −90° to 90° with the direction of the fiber bundle as the reference (0°). When the value of the convolution integral of the function (Formula 1) shown with the orientation detection filter F in the foregoing case and the function showing the fiber bundle is used as the output value, the output value within the rotating range will be as shown in the graph of FIG. 4A.

Upon referring to the output value shown in the graph of FIG. 4A, when the filter axis of the orientation detection filter F is 0°; that is, when the filter axis becomes a direction that is the same as the direction of the fiber bundle (in this example, direction that is obliquely upward and rightward), the output value becomes maximum. Consequently, this orientation detection filter F has characteristics that enable the detection of the direction of the fiber bundle.

Figure 4B:
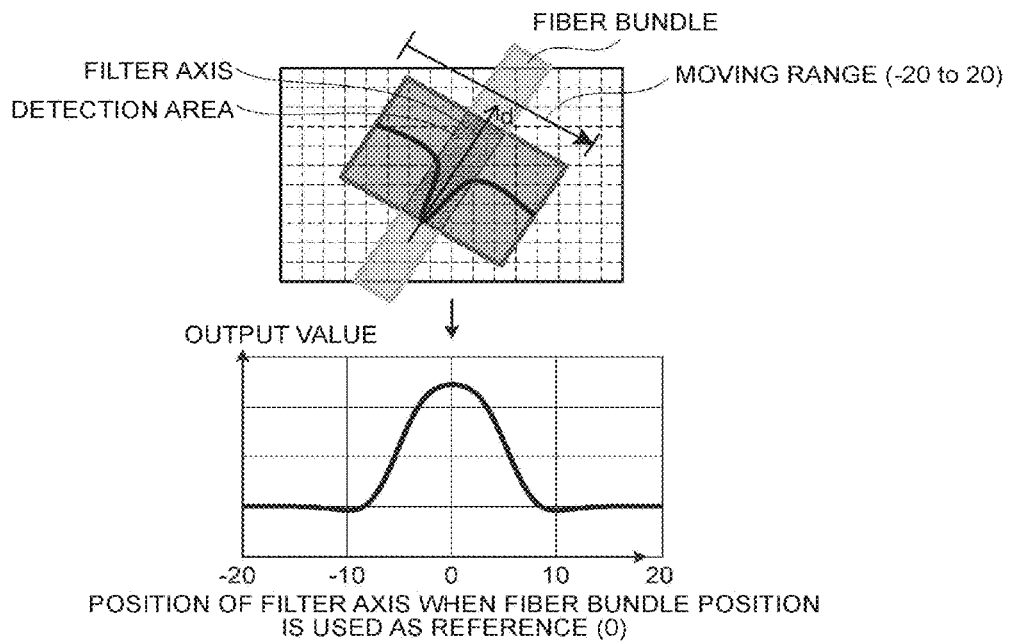
FIG. 4B is a conceptual diagram of the operation for detecting the center position of the fiber bundle.

FIG. 4B shows a conceptual diagram of the operation upon detecting the center position of the fiber bundle by using the orientation detection filter F. As shown in FIG. 4B, when the fiber bundle is facing a direction that is obliquely upward and rightward and positioned at the center of the target area, operation is performed so as to move the filter axis of the orientation detection filter F in a direction that is vertical to the fiber bundle direction within a range of, for example, −20 to 20 (unit is omitted) with the position of this fiber bundle as the reference. Here, when the value of the convolution integral of the function (Formula 1) shown with the orientation detection filter F and the function showing the fiber bundle is used as the output value, the output value within the range of parallel movement will be as shown in the graph of FIG. 4B.

Upon referring to the output value shown in the graph of FIG. 4B, when the filter axis of the orientation detection filter F is 0; that is, when the filter axis becomes a position that is the same as the position of the fiber bundle (in this example, center position of the target area), the output value becomes maximum. Consequently, this orientation detection filter F has characteristics that enable the detection of the center position of the fiber bundle.

As described above, the orientation detection filter F has characteristics of being able to detect the direction and center position of the fiber bundle. Thus, by using these characteristics of being able to detect the direction, in the orientation estimation processing (SP3), the orientation of the foreground pixels is estimated by changing the attitude control angles of the orientation detection filter F on the foreground pixels of the binary image G2 to search for the attitude control angles in which the output value will become maximum. The attitude control angles in which the output value will become maximum are represented in following Formula 2.

TABLE 2

$$\underset{\phi,\theta,\psi}{\operatorname{argmax}} (f_B * h_{\phi,\theta,\psi})(x) \quad (2)$$

$f_B$: Binary image
$h_{\phi,\theta,\psi}$: Orientation detection filter

Moreover, by using the characteristics of being able to detect the center position, in the center extraction processing (SP4), the center of the foreground pixel group is extracted by moving the orientation detection filter F in a direction that is vertical to the orientation direction within a prescribed search range relative to the foreground pixels in which the orientation thereof was estimated, and searching for the foreground pixels of a position in which the output value will become maximum.

Note that, in effect, since the input X-ray CT image G10 is a three-dimensional image, upon searching for the orientation, the attitude control angles of the orientation detection filter F on the foreground voxel are changed in order to search for the attitude control angles in which the output value will become maximum. Moreover, upon searching for the center position, the orientation detection filter F is moved in a direction that is vertical to the orientation direction within a predetermined range relative to the foreground voxel in which the orientation thereof was estimated in order to search for the position in which the output value will become maximum. As the pitch (resolution) of the attitude control angles, used may be, for instance, the upper half (or lower half) of the 5120 faces obtained by segmentalizing an icosahedron. In the foregoing case, the resolution will be 3.9 degrees.

Figure 5:
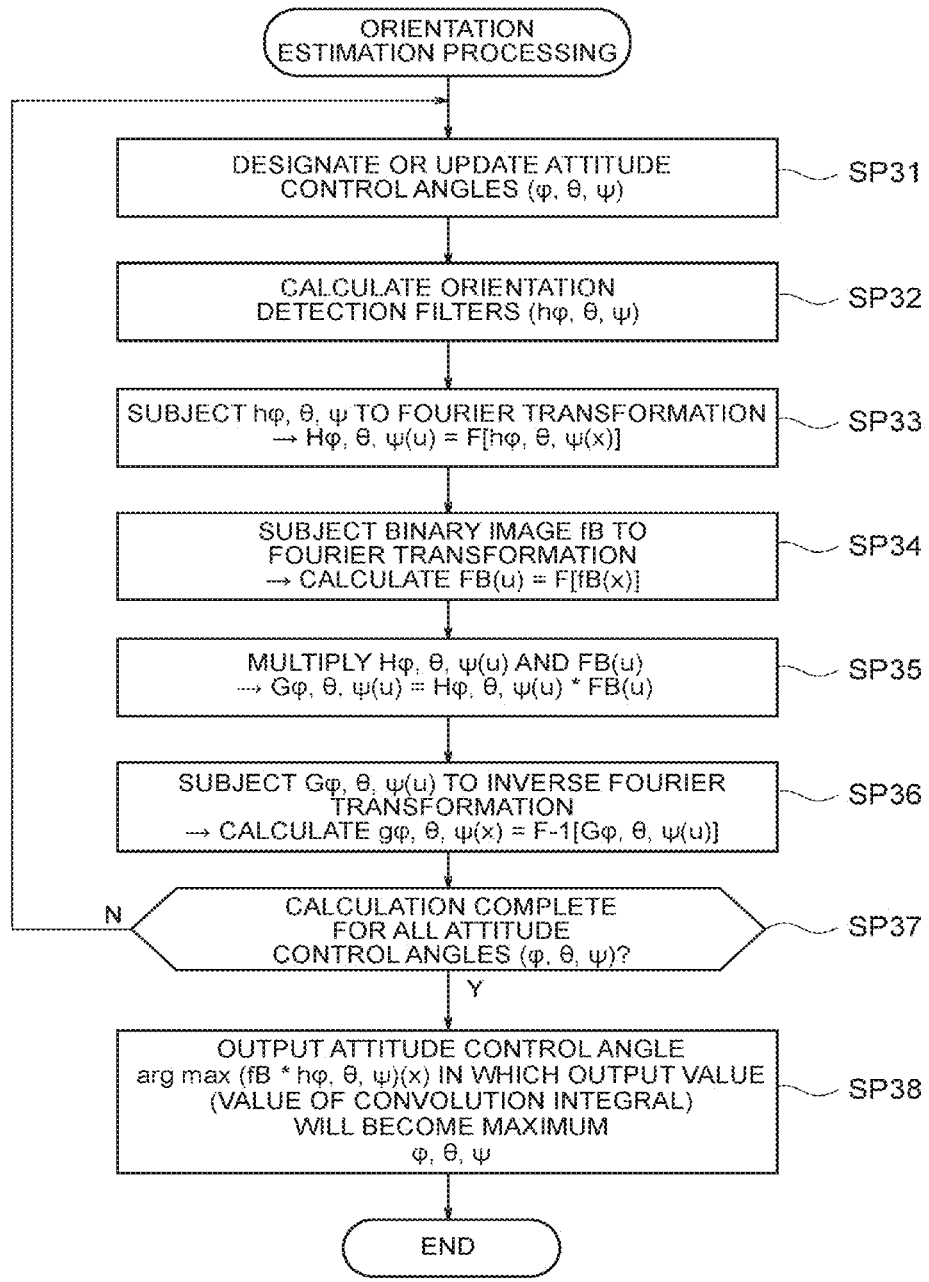
FIG. 5 is a detailed flowchart of the orientation estimation processing.

FIG. 5 shows the detailed processing routine of the orientation estimation processing. This orientation estimation processing is executed when the image analysis processing of FIG. 2 proceeds to step SP3.

Note that the orientation estimation processing explained here is the processing of changing the attitude control angles of the orientation detection filter F on the foreground pixels of the binary image G2, and estimating the attitude control angles in which the output value (value of convolution integral) will become maximum as the orientation of the target foreground pixels.

According to the convolution theorem, calculation of the convolution integral can be transformed into a simple multiplication of two functions by using Fourier transformation. In the foregoing case, it is possible to shorten the calculation time in comparison to a case of calculating the convolution integral as per its definition. Thus, in the orientation estimation processing of this embodiment, the two functions are simply multiplied after being subject to Fourier transformation, and the obtained result is subject to inverse Fourier transformation in order to calculate the convolution integral.

Foremost, the orientation estimation processing unit 152 designates the attitude control angles of the orientation detection filter F (SP31). Next, the orientation estimation processing unit 152 calculates the orientation detection filter F by inputting the designated attitude control angles into the orientation detection filter F (SP32). Next, the orientation estimation processing unit 152 subjects the orientation detection filter F to Fourier transformation (SP33).

Next, the orientation estimation processing unit 152 subjects the binary image G2 to Fourier transformation (SP34). Next, the orientation estimation processing unit 152 simply multiplies the orientation detection filter F that underwent Fourier transformation and the binary image that underwent Fourier transformation (SP35), and subject the result of such multiplication to inverse Fourier transformation (SP36). The orientation estimation processing unit 152 determines whether the calculation of all attitude control angles is complete (SP37).

When the orientation estimation processing unit 152 obtains a negative result in the determination of step SP37, it updates the attitude control angles and repeats the processing described above. Meanwhile, when the orientation estimation processing unit 152 obtains a positive result in the determination of step SP37, it outputs the attitude control angles in which the output value (value of convolution integral) will become maximum as the orientation of the target foreground pixels (SP38), and then ends this orientation estimation processing.

FIG. 6 shows the detailed processing routine of the center extraction processing. This center extraction processing is executed when the image analysis processing of FIG. 2 proceeds to step SP4.

Foremost, the center extraction processing unit 153 executes local maximum value search processing of searching for a local maximum value by moving the orientation detection filter F in a direction that is vertical to the estimated orientation with regard to the respective pixels in the foreground pixel group of the initial orientation estimation image G3 in which the orientation was estimated, and thereby creates a local maximum value identification image G31 (SP41).

Next, the center extraction processing unit 153 executes local maximum value residual processing of leaving only the foreground pixels of the local maximum value shown in the local maximum value identification image G31, creates a center extraction image G4 showing the thinned fiber bundle (SP42), and then ends this center extraction processing.

The image analyzing apparatus 1 can obtain the center extraction image G4 based on the processing (SP1 to SP4) heretofore. Thus, it is at least possible to estimate the orientation and extract the thinned foreground pixel group. Nevertheless, there are foreground pixels which fail to sufficiently satisfy the target orientation accuracy. Thus, in this embodiment, higher precision processing (SP5) is executed in order to more accurately estimate the orientation.

Specifically, the higher precision processing unit 154 partially differentiates the orientation detection filter F by the attitude control angles and calculates the gradient of the respective pixels of the foreground pixel group of the center extraction image G4, and executes processing of converging to the attitude control angles in which the calculation result will become maximum. The calculation formula of the gradient is represented with following Formula 3.

TABLE 3

$$(\phi_{k+1}, \theta_{k+1}, \psi_{k+1})^T = (\phi_k, \theta_k, \psi_k)^T + \alpha \nabla g \phi_k, \theta_k, \psi_k(x)$$

$$= (\phi_k, \theta_k, \psi_k)^T + \alpha \left( \frac{\partial g(x)}{\partial \phi_k}, \frac{\partial g(x)}{\partial g_k}, \frac{\partial g(x)}{\partial \phi_k} \right)^T$$

Provided $$\frac{\partial g_{\phi,\theta,\psi}(x)}{\partial \phi} = \frac{g_{\phi+h,\theta,\psi}(x) - g_{\phi-h,\theta,\psi}(x)}{2h} \quad (3)$$

$$\frac{\partial g_{\phi,\theta,\psi}(x)}{\partial \theta} = \frac{g_{\phi,\theta+h,\psi}(x) - g_{\phi,\theta-h,\psi}(x)}{2h}$$

$$\frac{\partial g_{\phi,\theta,\psi}(x)}{\partial \psi} = \frac{g_{\phi,\theta,\psi+h}(x) - g_{\phi,\theta,\psi-h}(x)}{2h}$$

FIG. 7 shows the detailed processing routine of the fiber bundle connection processing. This fiber bundle connection processing is executed when the image analysis processing of FIG. 2 proceeds to step SP6.

Foremost, the fiber bundle connection processing unit 155 searches for the foreground pixels in which the orientation direction is the same or similar within a neighborhood range among the respective foreground pixels in the higher precision image G5. The fiber bundle connection processing unit 155 executes clustering processing of grouping the foregoing pixel group in which the orientation direction is the same or similar as a result of the search, and thereby creates a clustered image G51 (SP61).

Next, the fiber bundle connection processing unit 155 executes connection point search processing of searching for the connection points by extending the searching area for searching for connectable pixels to a direction that is the same as the orientation direction of the foreground pixels of the starting point or the ending point based on the foreground pixels of the starting point or ending point among each of the grouped foreground pixel groups (SP62).

Next, if the searching areas that were respectively extended from the foreground pixels of the starting point or the ending point of different groups overlap, the fiber bundle connection processing unit 155 deems that the foreground pixels of the starting point or the ending point of different groups are pixels showing the same fiber bundle, executes connection processing of connecting these foreground pixels as the same group, thereby creates a fiber bundle connection image G6 (SP63), and then ends this fiber bundle connection processing.

The image analyzing apparatus 1 can create the fiber bundle connection image G6 based on the processing (SP1 to SP6) heretofore. In this embodiment, meander determination processing (SP7) is subsequently executed to determine the meandering amount. Specifically, the meander determination processing unit 156 applies an approximate straight line based on the least-squares method to the respective fiber bundles shown in the fiber bundle connection image G6. Then, the maximum value of the distance of the normal line drawn from the respective foreground pixels to the approximate straight line is determined as the meandering amount. When the meandering amount fall below a predetermined tolerance, it can be determined that the fiber bundles are oriented properly. The meandering amount is represented with following Formula 4.

Figure 8:
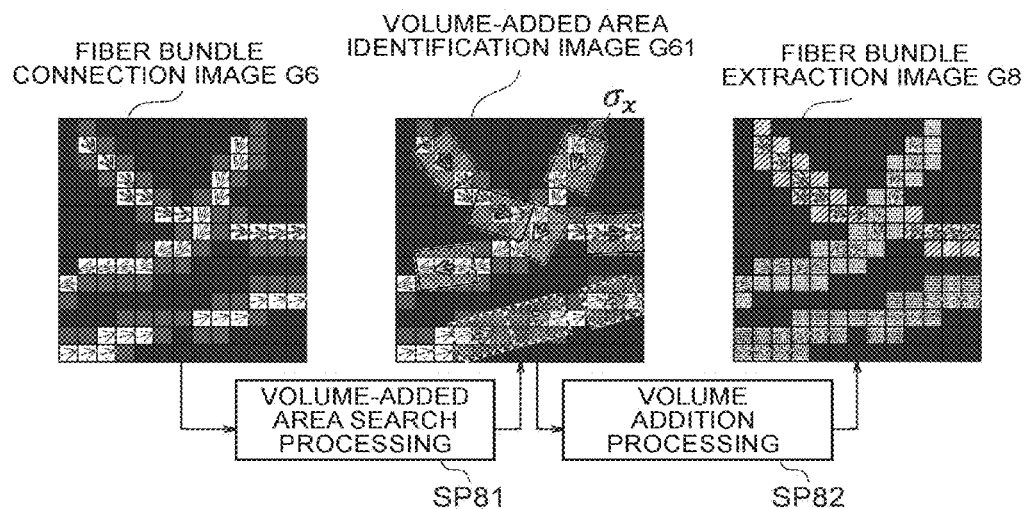
FIG. 8 is a detailed flowchart of the fiber bundle extraction image creation processing.

TABLE 4

$$s = \text{argmax}\, (|(x_k - x_g)| - |((x_k - x_g) * d)d|)$$

$$x_g = \frac{1}{N} \sum_{k=1}^{N} x_k$$

$$J = \Sigma_{k=1}^{N}(x_k - x_g)(x_k - x_g)^T \quad (4)$$

d: First eigenvector of J
N: Total number of center pixels (center voxel) of fiber bundle FIG. 8 shows the detailed processing routine of the fiber bundle extraction image creation processing. This fiber bundle extraction image creation processing is executed when the image analysis processing of FIG. 2 proceeds to step SP8.

In this fiber bundle extraction image creation processing, processing that is opposite to the processing of the center extraction processing (SP4) is executed. In other words, the fiber bundle extraction image creation processing unit 157 executes volume-added area search processing of arranging the orientation detection filter F in a direction that is the same as the estimated orientation to the respective foreground pixel groups of the fiber bundle connection image G6, and searching for the pixels containing within the calculating area of the orientation detection filter F (SP81).

Next, the fiber bundle extraction image creation processing unit 157 executes volume addition processing of extracting the pixels obtained as a result of searching for the pixels contained in the calculating area of the orientation detection filter F as the pixels of the fiber bundle, and adding the extracted pixels (SP82), and then ends this fiber bundle extraction image creation processing.

Figure 9:
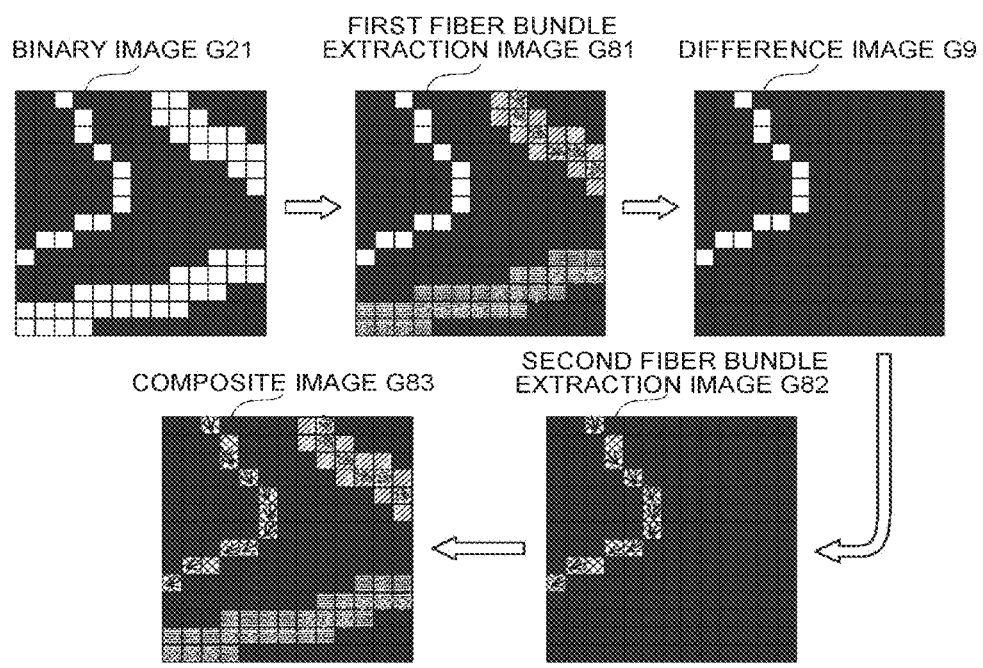
FIG. 9 is a flowchart showing another type of image analysis processing.

FIG. 9 shows the processing routine of another type of image analysis processing. The image analysis processing performed in this example differs from the image analysis processing shown in FIG. 2 with respect to the point that fiber bundles having different shapes are respectively extracted when an image containing fiber bundles of different shapes is input. In effect, a parameter for designating the anisotropy of the orientation detection filter F is changed to match the shape of the fiber bundle, and the image analysis processing (SP3 to SP8) of FIG. 2 is repeatedly executed.

Specifically, the various program stored in the memory 15 execute the image analysis processing (SP3 to SP8) of FIG. 2 to fiber bundles having the same shape when the binary image G21 showing a plurality of fiber bundle shapes is input, and thereby creates a first fiber bundle extraction image G81. Next, the various programs create a difference image G9 by dividing the foreground pixels in which the fiber bundles were extracted from the binary image G21.

Subsequently, the various programs change the parameter of the orientation detection filter F and re-execute the image analysis processing (SP3 to SP8) to the difference image G9 in order to create a second fiber bundle extraction image G82. Finally, the CPU 11 creates a composite image G83 by compositing the first fiber bundle extraction image G81 and the second fiber bundle extraction image G82, and thereby ends this processing.

(4) Image

Figure 10:
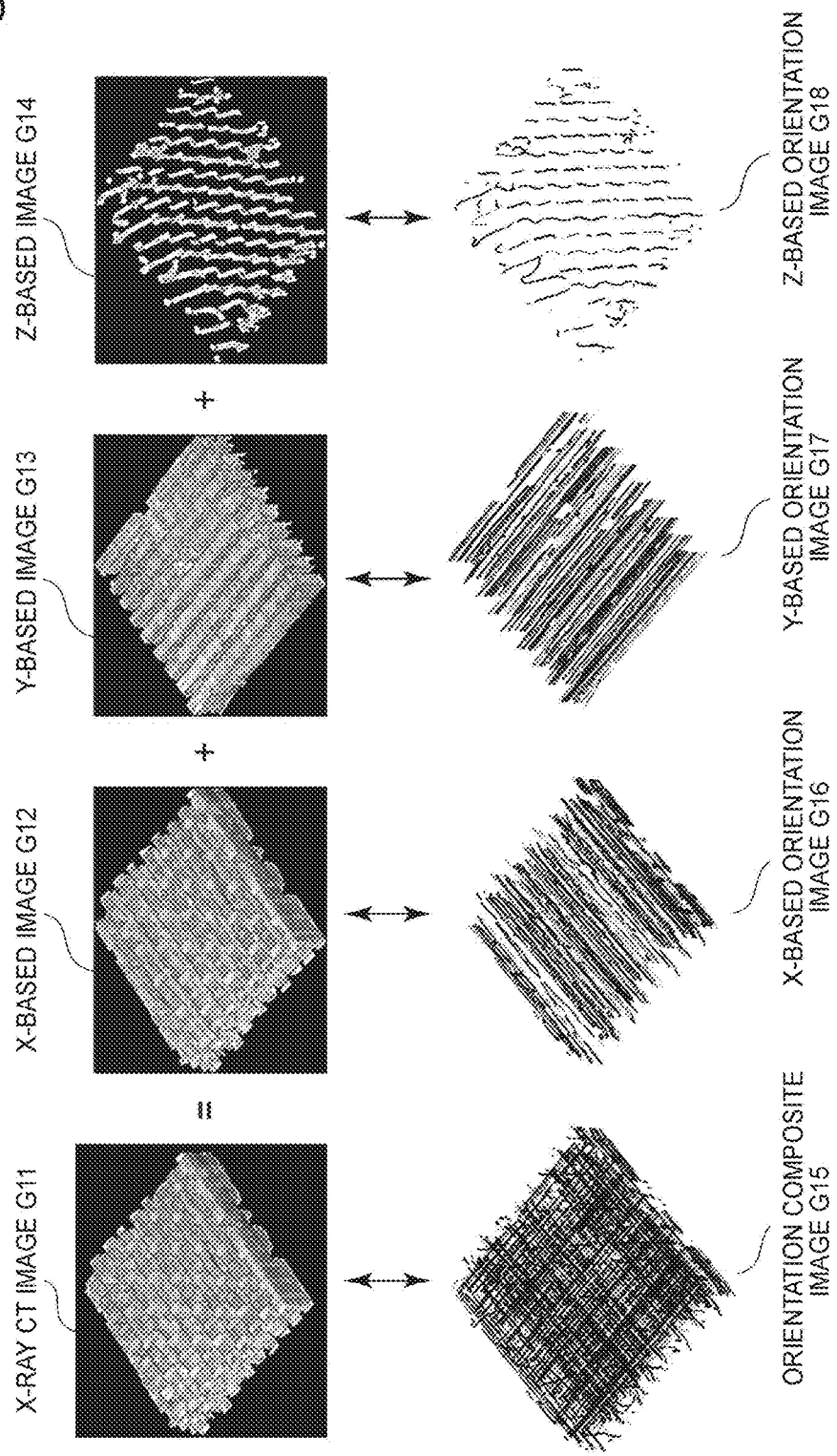
FIG. 10 is an analysis result in the case of inputting an X-ray CT image of a fabric woven via three-dimensional weaving.

FIG. 10 shows specific examples of the respective images that are actually obtained as a result of executing the image analysis processing described above. The X-ray CT image G11 is an image showing the fabric produced based on three-dimensional weaving that was input via the input unit 12. The X-based image G12 is an image created by extracting only the fiber bundles in which the orientation is in the X direction from the fabric in the X-ray CT image G11. The Y-based image G13 is an image created by extracting only the fiber bundles in which the orientation is in the Y direction from the fabric in the X-ray CT image G11. The Z-based image G14 is an image created by extracting only the fiber bundles in which the orientation is in the Z direction from the fabric in the X-ray CT image G11.

Moreover, the orientation composite image G15 is an image showing the orientation of the overall fabric which was created by compositing the X-based orientation image G16, the Y-based orientation image G17 and the Z-based orientation image G18. The X-based orientation image G16 is an image showing the center of the fiber bundles in which the orientation is in the X direction. The Y-based orientation image G17 is an image showing the center of the fiber bundles in which the orientation is in the Y direction. The Z-based orientation image G18 is an image showing the center of the fiber bundles in which the orientation is in the Z direction.

(5) Effects of this Embodiment

As described above, according to the image analyzing apparatus and program in this embodiment, since the orientation of the respective fiber bundles is automatically analyzed from the X-ray CT image of the fabric produced via three-dimensional weaving or plain weaving (or other weaving methods), the strength of CMC formed from this fabric can be easily evaluated based on the analysis result. Moreover, since the orientation of the respective fiber bundles can be analyzed even with an X-ray CT image having a relative low resolution, the imaging time of the X-ray CT image can be shortened. Thus, the present disclosure can be used for product inspection.

REFERENCE SIGNS LIST

1 Image analyzing apparatus
11 CPU
12 Input unit
13 Storage unit
14 Display unit
15 Memory
151 Binarization processing unit
152 Orientation estimation processing unit
153 Center extraction processing unit
154 Higher precision processing unit
155 Fiber bundle connection processing unit
156 Meander determination processing unit
157 Fiber bundle extraction image creation processing unit

The invention claimed is:

1. An image analyzing apparatus for analyzing an orientation of a fiber bundle from a three-dimensional image of a fiber-reinforced composite material, comprising:
   an input unit which inputs the three-dimensional image;
   a binarization processing unit which binarizes the input three-dimensional image and acquires a binary image;
   an orientation estimation processing unit which estimates each orientation of foreground pixels in the binary image based on an orientation detection filter having a parameter for causing a shape of a detected cross section to have anisotropy;
   a center extraction processing unit which extracts center pixel groups indicating a center of the fiber bundle from a foreground pixel group, in which the orientation thereof was estimated, based on the orientation detection filter;
   a fiber bundle connection processing unit which deems center pixels having a same or similar orientation to be a same fiber bundle with regard to the extracted center pixel group, and connects the center pixels indicating the same fiber bundle; and
   a meander determination processing unit which calculates a meandering amount of the connected center pixel group indicating the same fiber bundle.

2. The image analyzing apparatus according to claim 1, wherein the orientation estimation processing unit changes attitude control angles of the orientation detection filter on the foreground pixels, searches for the attitude control angles in which a value of a convolution integral of a function indicated by the orientation detection filter and a function indicating the foreground pixels becomes maximum, and estimates a filter axial direction of the orientation detection filter in the attitude control angles in which the value of the convolution integral becomes maximum as the orientation of the foreground pixels.

3. The image analyzing apparatus according to claim 1, wherein the center extraction processing unit moves the orientation detection filter on the foreground pixel group in a direction that is vertical to the estimated orientation direction, searches for a position of the orientation detection filter in which a value of a convolution integral of a function indicated by the orientation detection filter and a function indicating the foreground pixel group becomes maximum, and extracts, as the center pixels, pixels on the foreground pixel group corresponding to the position of the orientation detection filter in which the value of the convolution integral becomes maximum.

4. The image analyzing apparatus according to claim 1, wherein the fiber bundle connection processing unit groups successive center pixel groups that show a same or similar orientation direction with regard to the center pixel groups, extends a searching area to a direction that is the same as the orientation of the pixels of a starting point or an ending point of the grouped center pixel groups, and, when the extended searching areas overlap, deems that the pixels of the starting point or ending point belonging to different groups as pixels indicating the same fiber bundle, and connects the center pixels indicating the same fiber bundle by connecting the pixels of the starting point or ending point.

5. The image analyzing apparatus according to claim 1, wherein the meander determination processing unit calculates an appropriate straight line of the center pixel group indicating the same fiber bundle based on a least-squares method, applies the calculated approximate straight line to the center pixel group, and calculates, as the meandering amount, a maximum value among distances of a normal line lowered to the appropriate straight line from each of the center pixel groups.

6. The image analyzing apparatus according to claim 1, further comprising:
a higher precision processing unit which corrects each orientation of the center pixels based on the orientation detection filter and a gradient method after the center extraction processing unit extracts the center pixels from the foreground pixel group.

7. The image analyzing apparatus according to claim 1, further comprising:
a fiber bundle extraction image creation processing unit which creates a fiber bundle extraction image by adding the foregoing pixels indicating the fiber bundle after the fiber bundle connection processing unit connects the center pixels.

8. The image analyzing apparatus according to claim 1, wherein the three-dimensional image of the fiber-reinforced composite material is an image obtained by imaging a fabric produced via three-dimensional weaving or plain weaving with an X-ray CT device.

9. A non-transitory computer-readable medium storing computer readable instructions thereon for analyzing an orientation of a fiber bundle from a three-dimensional image of a fiber-reinforced composite material, that when executed by a computer cause the computer to perform a method comprising:
inputting the three-dimensional image;
binarizing the input three-dimensional image and acquiring a binary image;
estimating each orientation of foreground pixels in the binary image based on an orientation detection filter having a parameter for causing a shape of a detected cross section to have anisotropy;
extracting center pixel groups indicating a center of the fiber bundle from a foreground pixel group, in which the orientation thereof was estimated, based on the orientation detection filter;
deeming center pixels having a same or similar orientation to be a same fiber bundle with regard to the extracted center pixel group, and connecting the center pixels indicating the same fiber bundle; and
calculating a meandering amount of the connected center pixel group indicating the same fiber bundle.

10. The non-transitory computer-readable medium according to claim 9, further comprising:
correcting each orientation of the center pixels based on the orientation detection filter and a gradient method after extracting center pixel groups; and
creating a fiber bundle extraction image by adding the foregoing pixels indicating the fiber bundle after connecting the center pixels.

* * * * *